(12) United States Patent
Meyer et al.

(10) Patent No.: US 7,651,387 B2
(45) Date of Patent: Jan. 26, 2010

(54) APPARATUS AND METHOD FOR PROCESSING BOVINE PERICARDIUM

(75) Inventors: Peter French Meyer, Napier (NZ); Brian Geoffery Bennett, Napier (NZ)

(73) Assignee: Southern Lights Ventures 2002 Limited, Napier (NZ)

( * ) Notice: Subject to any disclaimer, the term of this patent is extended or adjusted under 35 U.S.C. 154(b) by 0 days.

(21) Appl. No.: 12/078,328

(22) Filed: Mar. 28, 2008

(65) Prior Publication Data

US 2009/0247061 A1 Oct. 1, 2009

(51) Int. Cl.
*A22C 17/16* (2006.01)
(52) U.S. Cl. ..................................... 452/134
(58) Field of Classification Search ............... 452/134, 452/174; 66/66, 24–26
See application file for complete search history.

(56) References Cited

U.S. PATENT DOCUMENTS

| 1,644,976 | A |   | 10/1927 | Bredown |       |
|-----------|---|---|---------|---------|-------|
| 3,198,408 | A | * | 8/1965  | Benner  | 223/66|
| 3,300,108 | A | * | 1/1967  | Schumer | 223/66|
| 3,320,681 | A | * | 5/1967  | Watlington | 34/90 |
| 3,653,563 | A | * | 4/1972  | Russ    | 223/66|
| D351,745  | S | * | 10/1994 | Seifert | D6/415|
| 5,413,798 | A |   | 5/1995  | Scholl et al. | |
| 6,352,708 | B1|   | 3/2002  | Duran et al. | |
| 6,463,332 | B1|   | 10/2002 | Aldrich | |
| 6,475,239 | B1|   | 11/2002 | Campbell et al. | |
| 6,545,042 | B2|   | 4/2003  | Sung et al. | |
| 6,585,635 | B1|   | 7/2003  | Aldrich | |
| 6,660,265 | B1|   | 12/2003 | Chen et al. | |
| 7,175,517 | B1| * | 2/2007  | Weakley | 452/149 |
| 2006/0074397 | A1 | | 4/2006 | Shimada | |
| 2007/0020245 | A1 | | 1/2007 | Trott | |
| 2007/0269478 | A1 | | 11/2007 | Piconi et al. | |

FOREIGN PATENT DOCUMENTS

| CN | 1279114    | 10/2006 |
| DE | 590 606    | 1/1934  |
| FR | 646 288    | 11/1928 |
| FR | 690 832    | 9/1930  |
| GB | 281628     | 1/1928  |
| WO | WO 99/48540 | 9/1999 |

OTHER PUBLICATIONS

Hiester et al. "Optimal bovine pericardial tissue selection sites. I. Fiber architecture and tissue thickness mearsurements." Journal of Biomedical Materials Research, vol. 39 (1998), pp. 207-214.
International Search Report dated Sep. 30, 2009.

* cited by examiner

*Primary Examiner*—Thomas Price
(74) *Attorney, Agent, or Firm*—Jacobson Holman PLLC

(57) ABSTRACT

An apparatus for use in processing "raw" pericardium. The apparatus includes a mold having a generally hemispheroid dome and a support base upon which the mold is mounted. The hemispheroid dome has a diameter suitable for stretching a pericardium over the dome. Also, a method for processing "raw" pericardium. The method involves stretching raw pericardium over a mold such that the pericardium conforms to the shape of the mold and the mold stretches the pericardium. This is followed by separating at least some of the fat layer off the pericardial tissue layer where the pericardium is mounted over the mold and finally removing fat from the total pericardium surface.

16 Claims, 11 Drawing Sheets under the US 7,651,387 B2

APPARATUS AND METHOD FOR PROCESSING BOVINE PERICARDIUM

FIELD OF THE INVENTION

The present invention relates to an apparatus and method for processing bovine pericardium and in particular producing high quality bovine pericardium tissue.

BACKGROUND TO THE INVENTION

Bovine pericardium is used in xenograft technology, including for example, for the manufacture of artificial heart valves which are implantable into humans. "Raw" bovine pericardium is harvested from slaughtered animals within an abattoir. The "raw" pericardium is covered with a layer of thick fat. The harvested pericardium undergoes a cleaning process in which the fat layer is removed. The "raw" pericardium is dipped in cold saline bath, so as to congeal the fat. The fat is removed by placing the pericardium on a board and pulling, scrapping and tearing the fat off.

U.S. Pat. No. 6,463,332 B1 discloses a scrapping tool for removal of fat from a human pericardium during an operating procedure in which the patient's pericardium is modified to reduce the risk of heart attacks. This same tool could conceivably be used to scrape the fat off Bovine Pericardium. The current employed cleaning process for bovine pericardium produces low quality pericardium. The pericardium becomes mushy due to the blunt trauma applied to it during the cleaning process. This results in a high proportion of harvested pericardium being rejected.

SUMMARY OF THE INVENTION

It is an object of the present invention to provide an apparatus and method for producing firmer, higher quality pericardium resulting from this method as compared to the current processing techniques or at least provide the processing and the xenograft industry with a useful choice.

In a first aspect the invention may broadly be said to consist in an apparatus for the processing "raw" pericardium comprising:
a mold including a generally hemispheroidal dome,
a support base upon which the mold is mounted, and
the hemispheroid dome having a diameter suitable for stretching a pericardium over the dome.

Preferably the hemispheroid dome is a prolate hemispheroid dome.

Preferably the hemispheroid dome has a diameter between 10 cm and 30 cm at the widest point.

Preferably the mold is mounted upon a support base.

Preferably the support base includes a spike extending from the support base.

Preferably the spike connects into a hole in the mold.

Preferably the hole in the mold is centered about the major axis of the hemispheroid dome.

Preferably the support base has a plurality of straight side edges.

Preferably the support base is made from a dense material so as to provide the dome with stability.

Preferably the dome is rotatable on the support base about the major axis of the dome.

Preferably the hemispheroid dome is constructed from a material having a surface which provides some gripping force on tissue.

More preferably the mold is made of for example high density polyethylene (HDPE).

More preferably the mold is constructed out of materials which are steriliseable and are suitable for use in an abattoir.

In a second aspect the invention provides a method for processing "raw" pericardiurn comprising:
stretching "raw" pericardium over a mold, such that the pericardium conforms to the shape of the mold and the mold stretches the pericardium;
separating at least some of the fat layer off the pericardial tissue layer where the pericardium is mounted on the mold; and
removing fat from the total pericardium surface.

Preferably such method includes the step of cutting along the pericardium, starting at the opening for the aorta, vena cava and pulmonary artery, to obtain a flat sheet of pericardium.

Preferably the method includes the step of, before "raw" pericardium is stretched over the mold, holding the raw pericardium in a cold saline bath until the fat covering pericardium has stiffened.

Preferably a knife or hands are used to remove or separate said fat layer from said pericardium.

Preferably said method includes rotating the mold to work the fat layer away from the pericardium progressively toward the arterial opening.

BRIEF DESCRIPTION OF DRAWINGS

One preferred embodiment of the invention is described with reference to accompanying figures.

For the sake of clarity the fat is cross hatched, the pericardium is straight hatched and the mold is unhatched.

Figure 3:
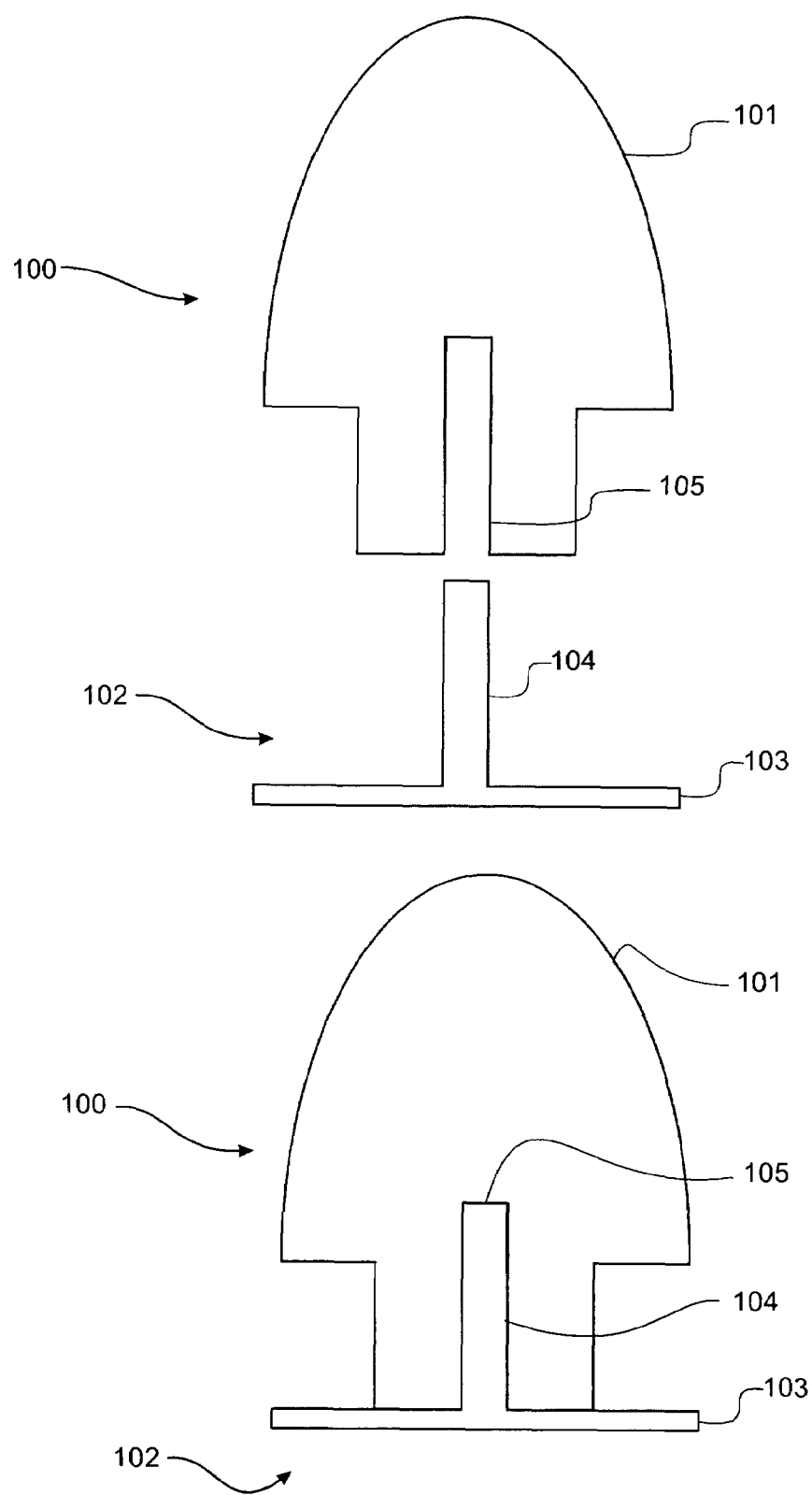

FIG. 3 shows a cross section view of the mold and support base, particularly demonstrating the connection between the mold and support base via a shaft and hole connection

DETAILED DESCRIPTION OF THE PREFERRED EMBODIMENTS

Figure 1:
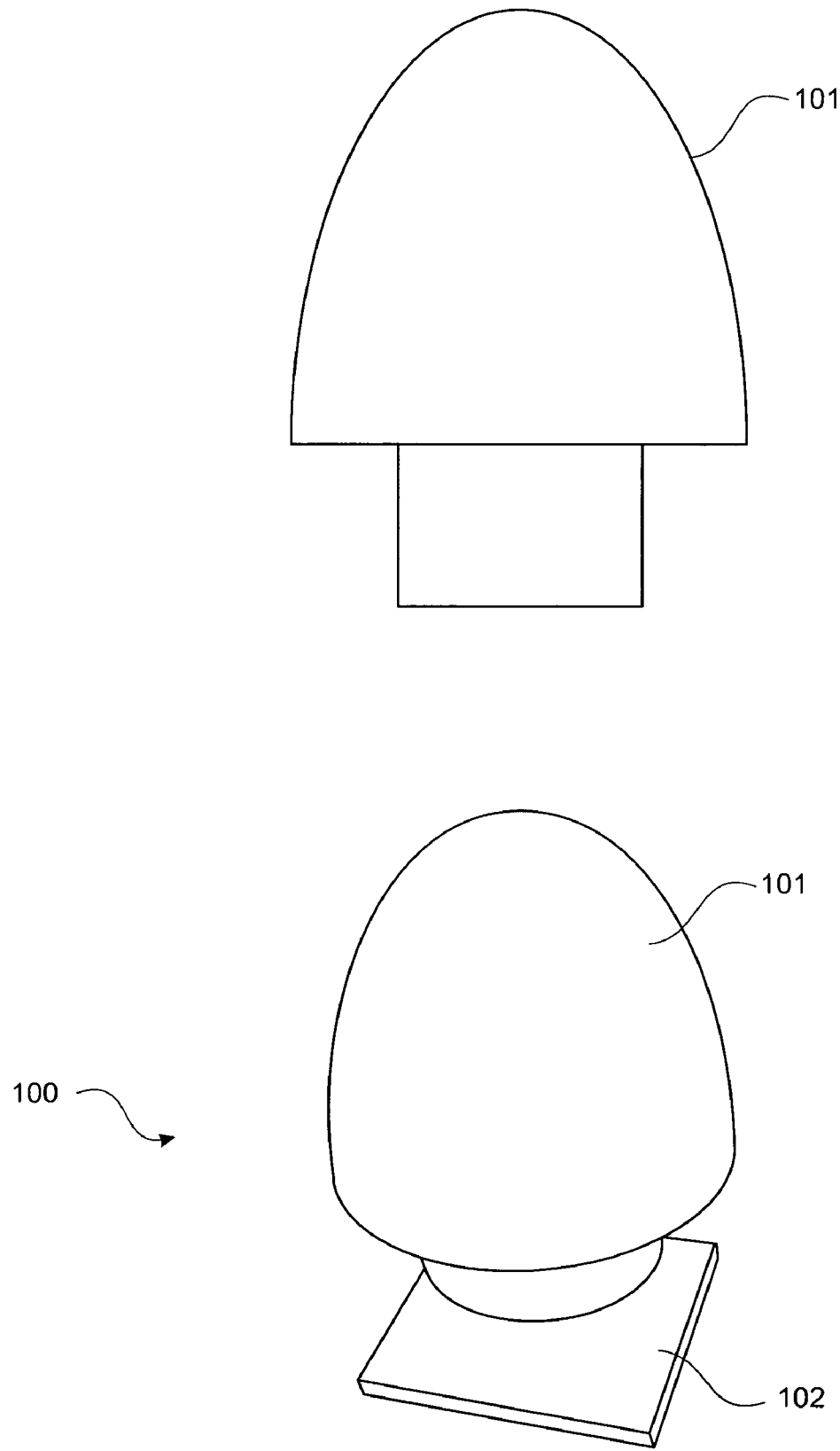
FIG. 1 is a side view and perspective view of the pericardium processing apparatus.

FIG. 1 is a view of the preferred apparatus according to the present invention is used for the processing of "raw" pericardium. Typically the defatting process is carried out at the abattoir where the pericardium is harvested.

In the preferred embodiment the apparatus dome is approximately a prolate hemispheroid. A prolate hemispheroid is a 2-dimensional ellipse revolved about its major axis to essentially form a 3-dimensional ellipse. This 3-dimensional ellipse is called a prolate spheroid, and a half of such a prolate spheroid is called a prolate hemispheroid. The mold is not limited to being of a prolate hemispheroid shape. A variety of other shapes like a sphere, hemisphere, oblate hemispheroid, ovoid, conical or any other curvilinear shape may be used in the construction of the mold. The illustrated shape is chosen to conform to an average contour of a bovine pericardium sac.

In the preferred embodiment the hemispheroid dome 101 has a diameter between 10 cm and 30 cm at its widest point, which runs along its minor axis, most preferably the maximum diameter is about 35 cm. In the preferred embodiment the height of the hemispheroid dome is approximately 20 cm to 40 cm at its highest point.

FIG. 3 shows a cross section view of the mold 100 and support base 102. The mold is mounted on a support base 102. The support base 102 preferably includes a shaft 104 which extends from a base 103.

Preferably the shaft connects into a hole 105 within the mold. Preferably the hole is centered upon the major axis of the hemispheroid dome but is not limited to this. The attachment hole can be anywhere on the mold. The connection could also take a variety of forms, for example a bolt, screw, pin and many other forms which would be obvious to a person skilled in the art. However a simple shaft and hole is preferred due to the need for effective cleaning and sterilization. More preferably the hole 105 is 16 mm in diameter and extends 150 mm deep into the mold.

Preferably the support base 102 has a plurality of straight side edges. Ideally the base should be a rectangle for example a square, but is not limited to being a rectangle. The support base 102 can take the form of any polygon.

In the preferred embodiment the support base 102 is made from a dense material such as stainless steel or wood but not being limited to these materials. The dense material used for the construction of the support base 102, provides stability to the mold from tipping, slipping sliding and other motion which would hinder the processing of "raw" pericardium.

Preferably the hemispheroid dome 101 is rotatable on the support base 102. In the preferred embodiment this is enabled by the shaft and bolt connection. Preferably the hemispheroid dome 101 is rotatable about the major axis of the hemispheroid dome.

In the preferred embodiment illustrated in FIG. 1 the mold 100 is constructed from a material which provides some gripping force on tissue. Preferably this material is high density polyethylene (HDPE). The mold 100 could be constructed out of any cutting board material like stainless steel, wood or any other suitable polymer. Preferably these materials used to construct the mold 100 are also sterilizable and suitable for use in an abattoir.

Figure 2A:
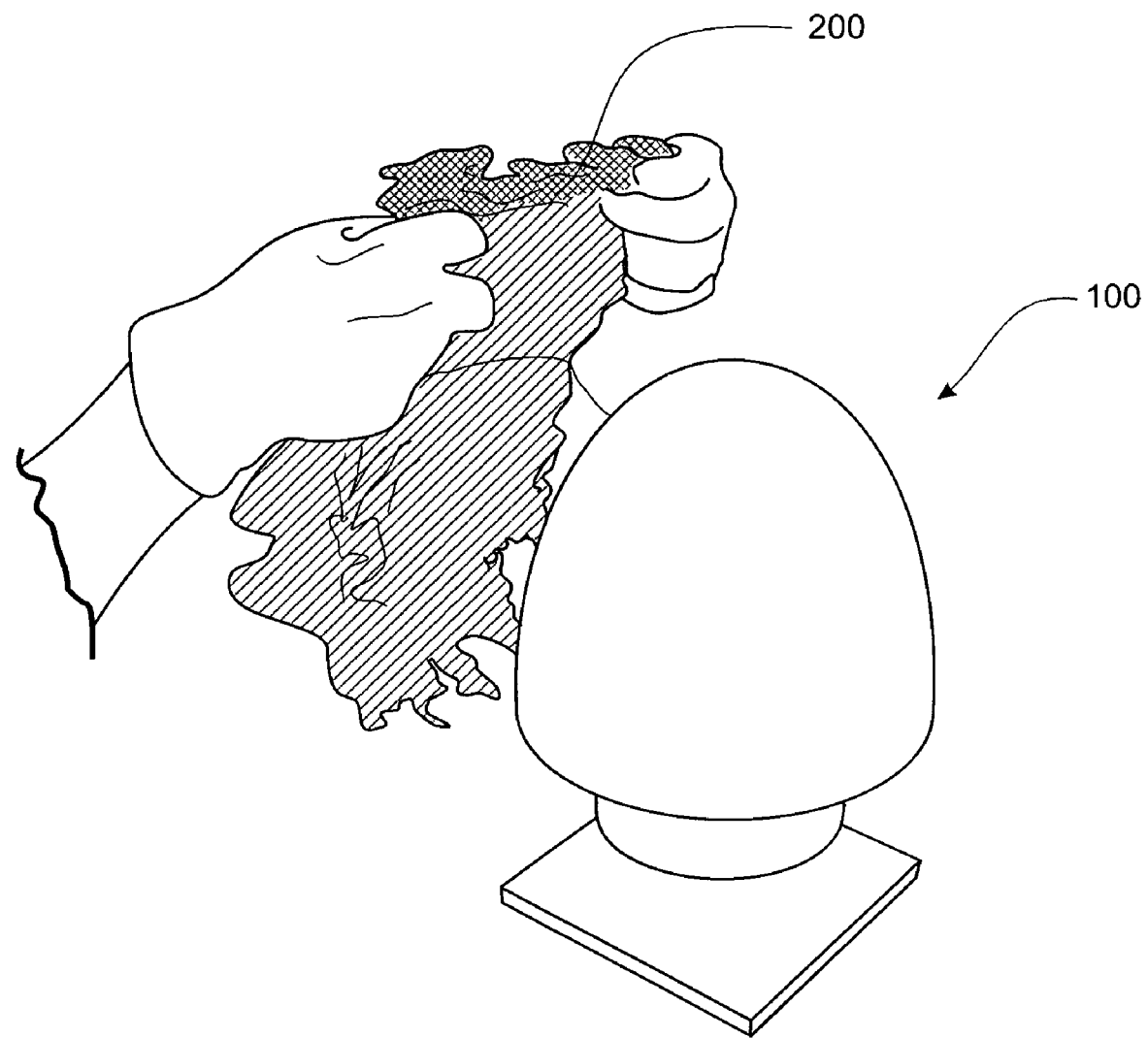
FIG. 2a shows the "raw" pericardium about to be placed over the mold.
Figure 2B:
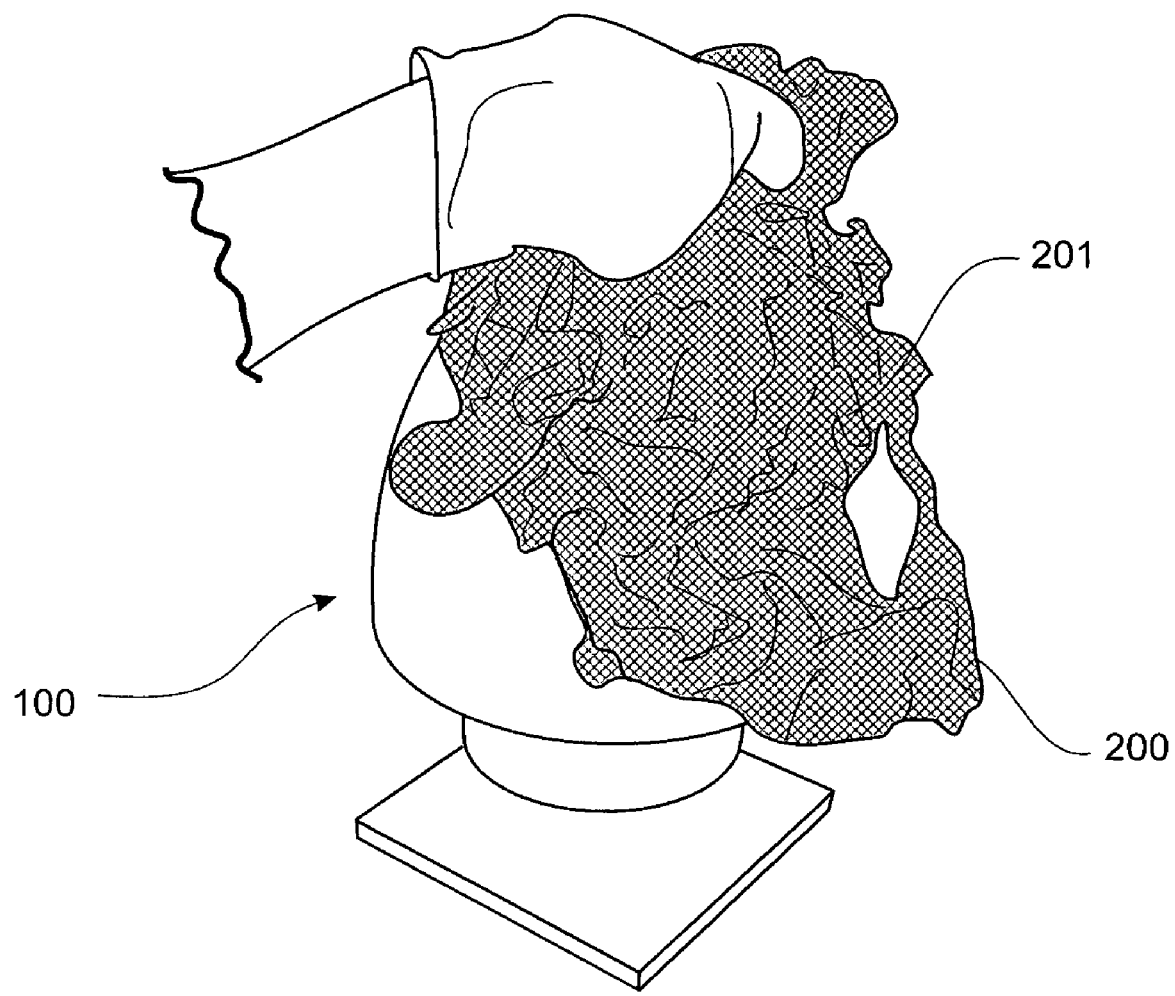
FIG. 2b shows the "raw" pericardium being stretched over the mold.
Figure 2C:
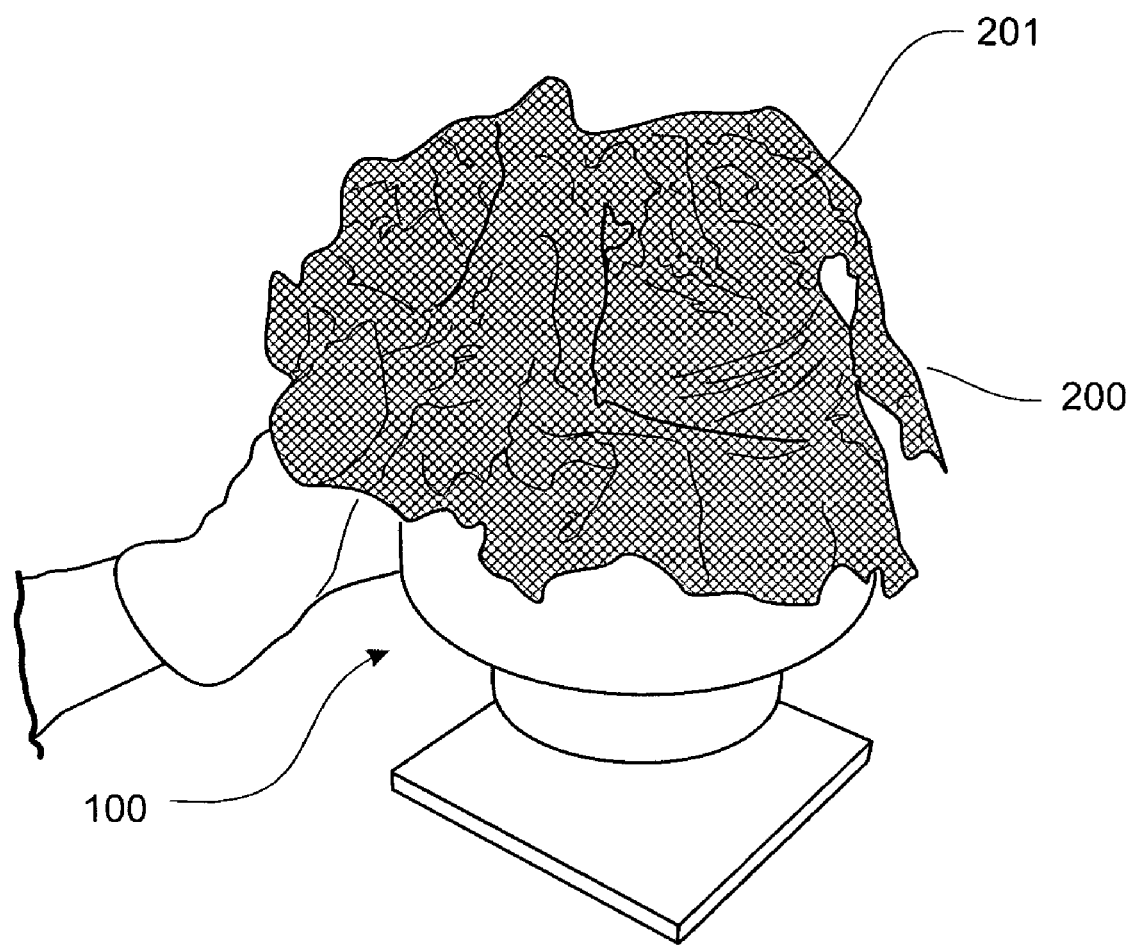
FIG. 2c shows the "raw" pericardium after it is stretched over the mold.

FIGS. 2a to 2i illustrate the method for processing "raw" pericardium. FIG. 2a shows the mold 100 and the pericardium 200 about to be stretched over the mold. FIGS. 2b and 2c illustrate how the pericardium is placed on the mold and stretched over the mold and how the mold stretches the pericardium. FIGS. 2b and 2c show the fat layer 201 covering the pericardium 200.

Figure 2D:
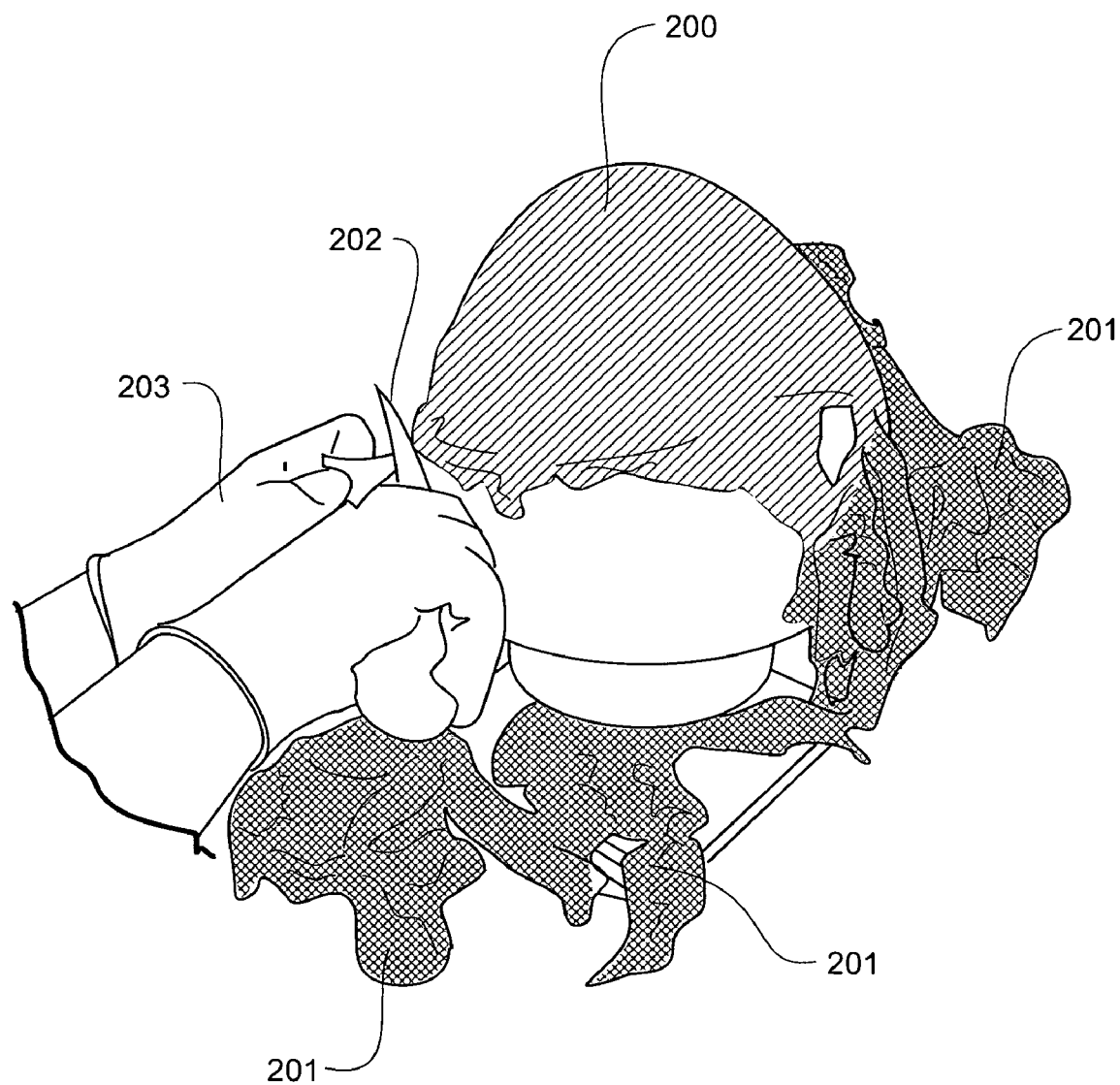
FIG. 2d shows the surface fat being removed from the pericardium, exposing the pericardium layer.
Figure 2E:
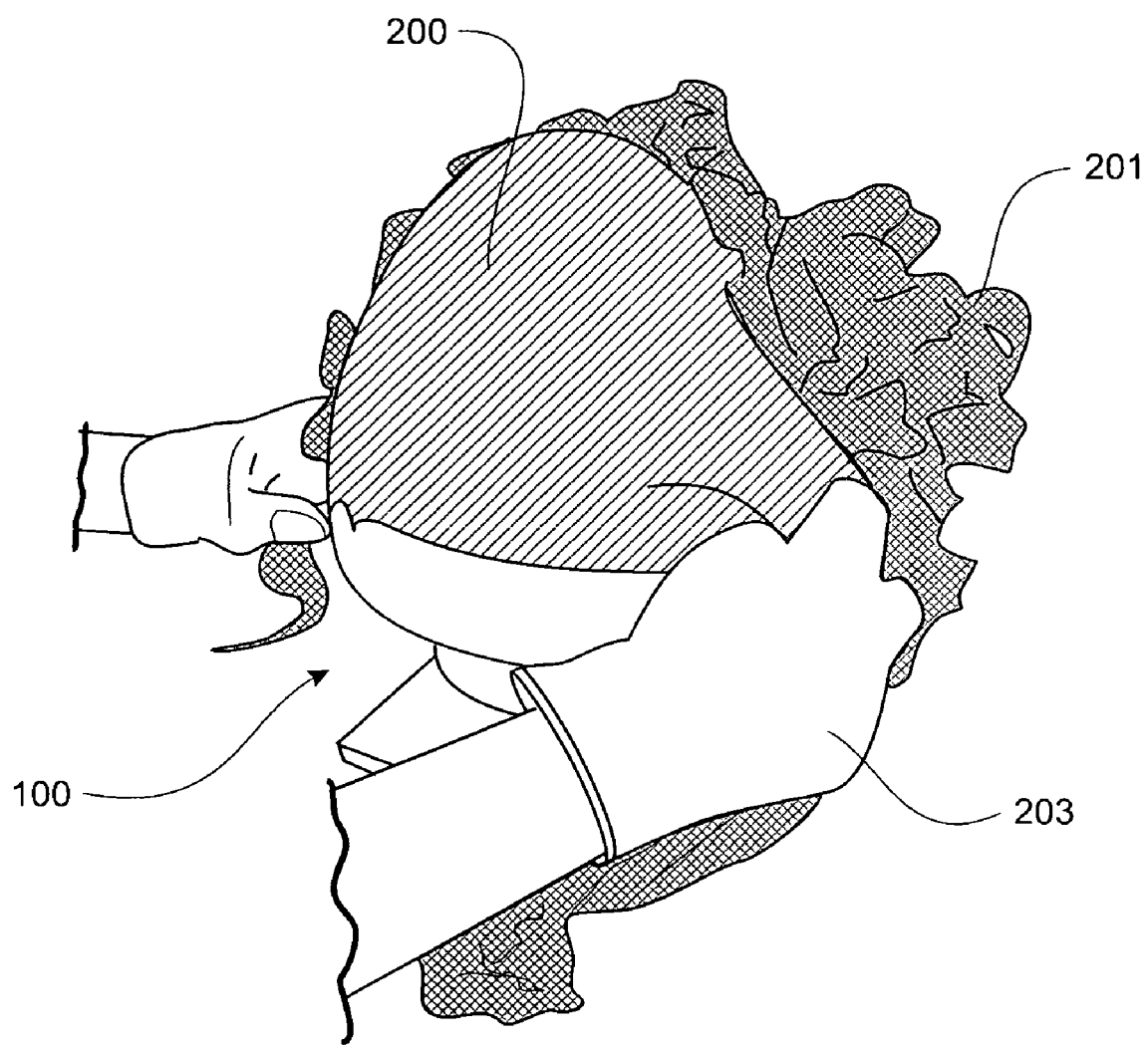
FIG. 2e shows the surface fat being cut off the pericardium layer.

FIGS. 2d and 2e show the fat layer being separated off the pericardial tissue while the pericardium is mounted over the mold. The process involves rotating the mold 100 to work the fat layer away from the pericardium progressively toward the arterial opening. FIGS. 2d and 2e also show the removal of the fat 201 from the total pericardium 200 surface. The exposed "cleaned" pericardium is shown in FIGS. 2d and 2e. Preferably the method of removing fat uses a knife 202 or hands 203 as shown in FIGS. 2d and 2e, but is not restricted to these. Any other tools can be used like a scraper, tongs or any other abattoir equipment and are quite obvious to a person skilled in the art. The present invention involves the general concept of fat removal with aid of the mold 100 described in FIG. 1.

Figure 2F:
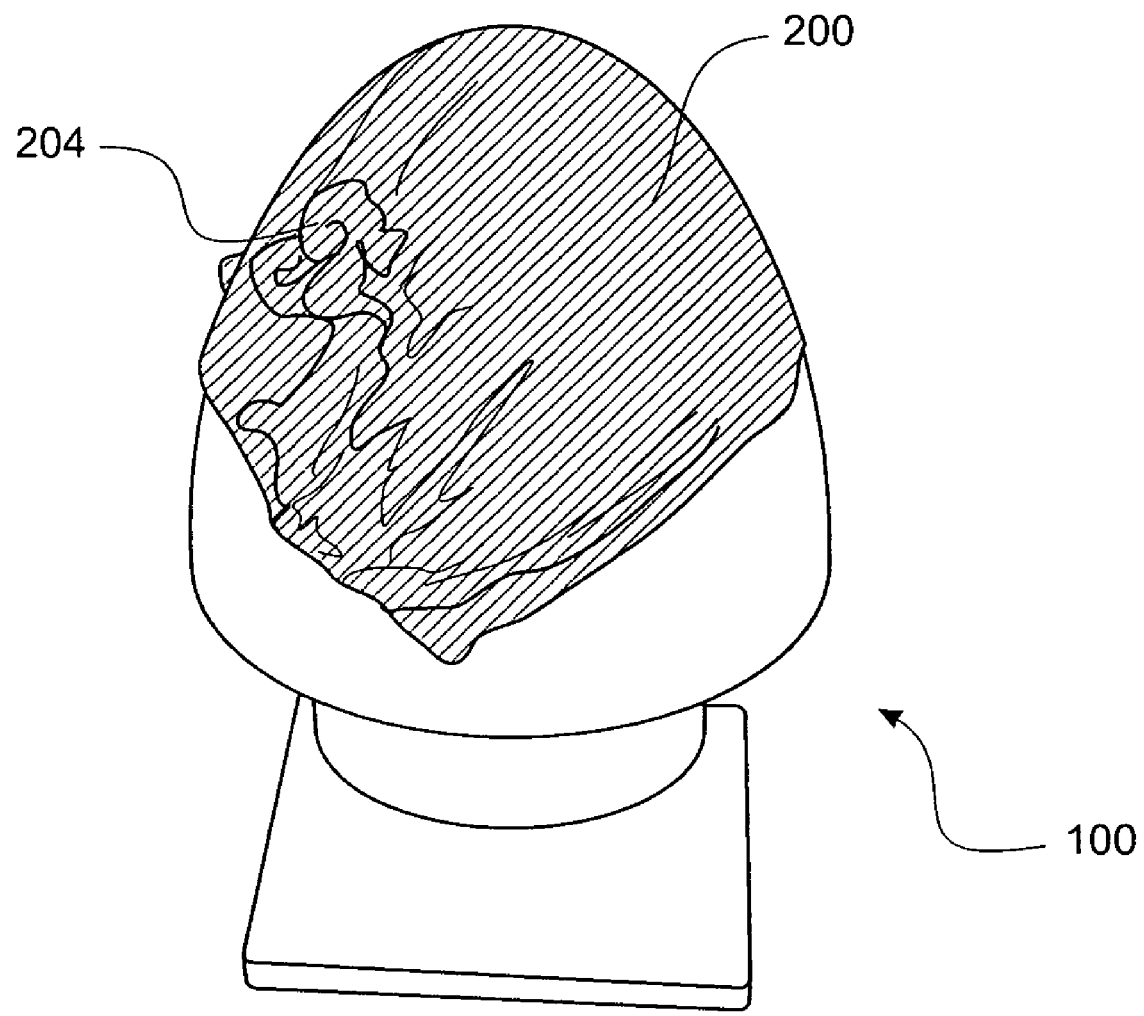
FIG. 2f shows the cleaned pericardium layer and the opening for the aorta, vena cava and the pulmonary artery.
Figure 2G:
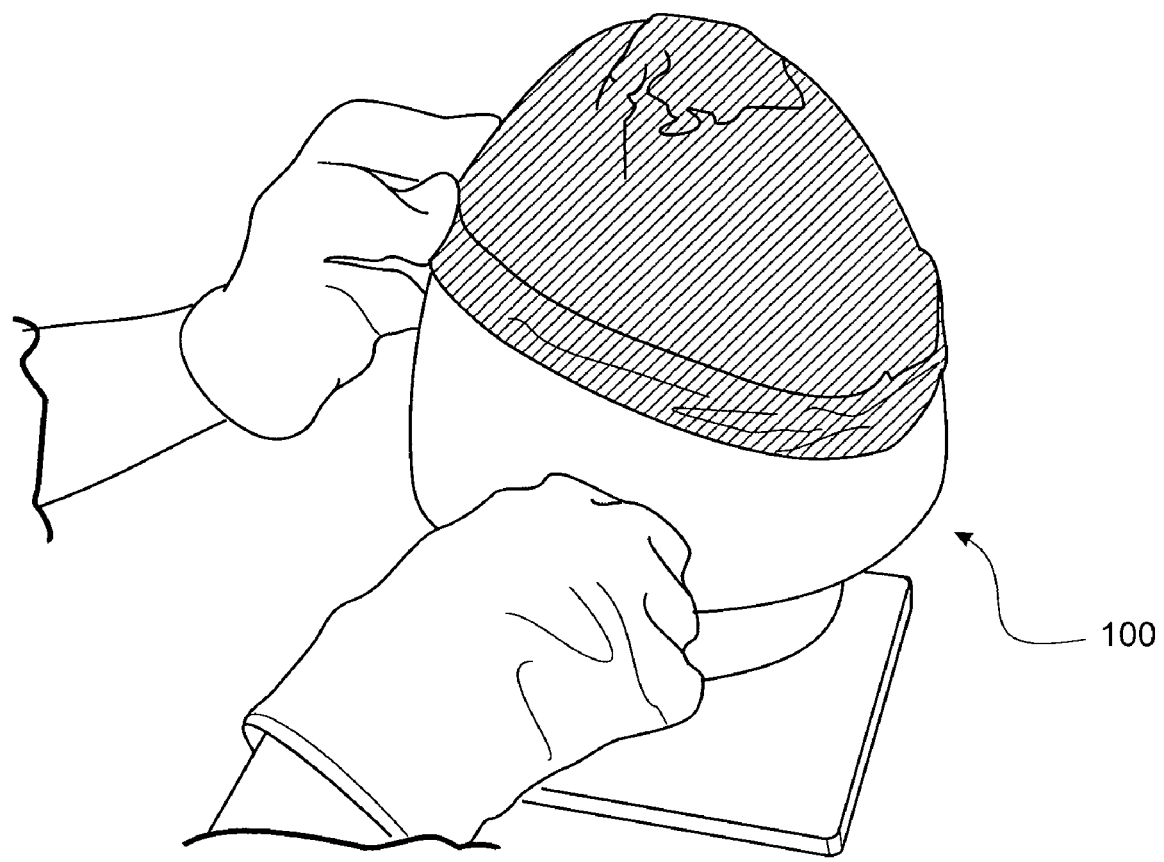
FIG. 2g shows the cleaned pericardium being removed from the mold.

FIG. 2f shows the cleaned pericardium with the entire surface fat layer 201 being removed. The opening for the aorta, vena cava and pulmonary artery is shown by 204 in FIG. 2f FIG. 2g shows the "cleaned" pericardium being removed from the mold 100.

Figure 2H:
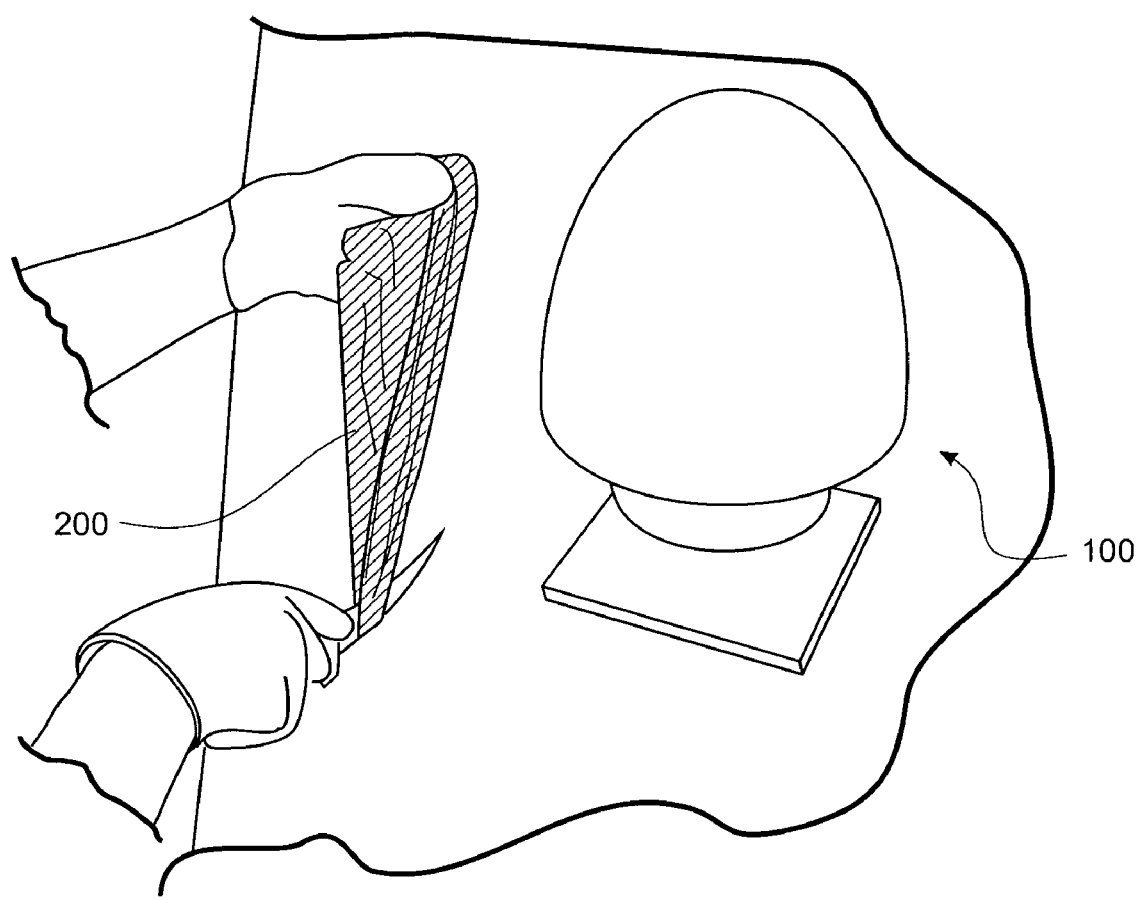
FIG. 2h shows the cleaned pericardium being cut along the opening for the aorta, vena cava and the pulmonary artery.
Figure 2I:
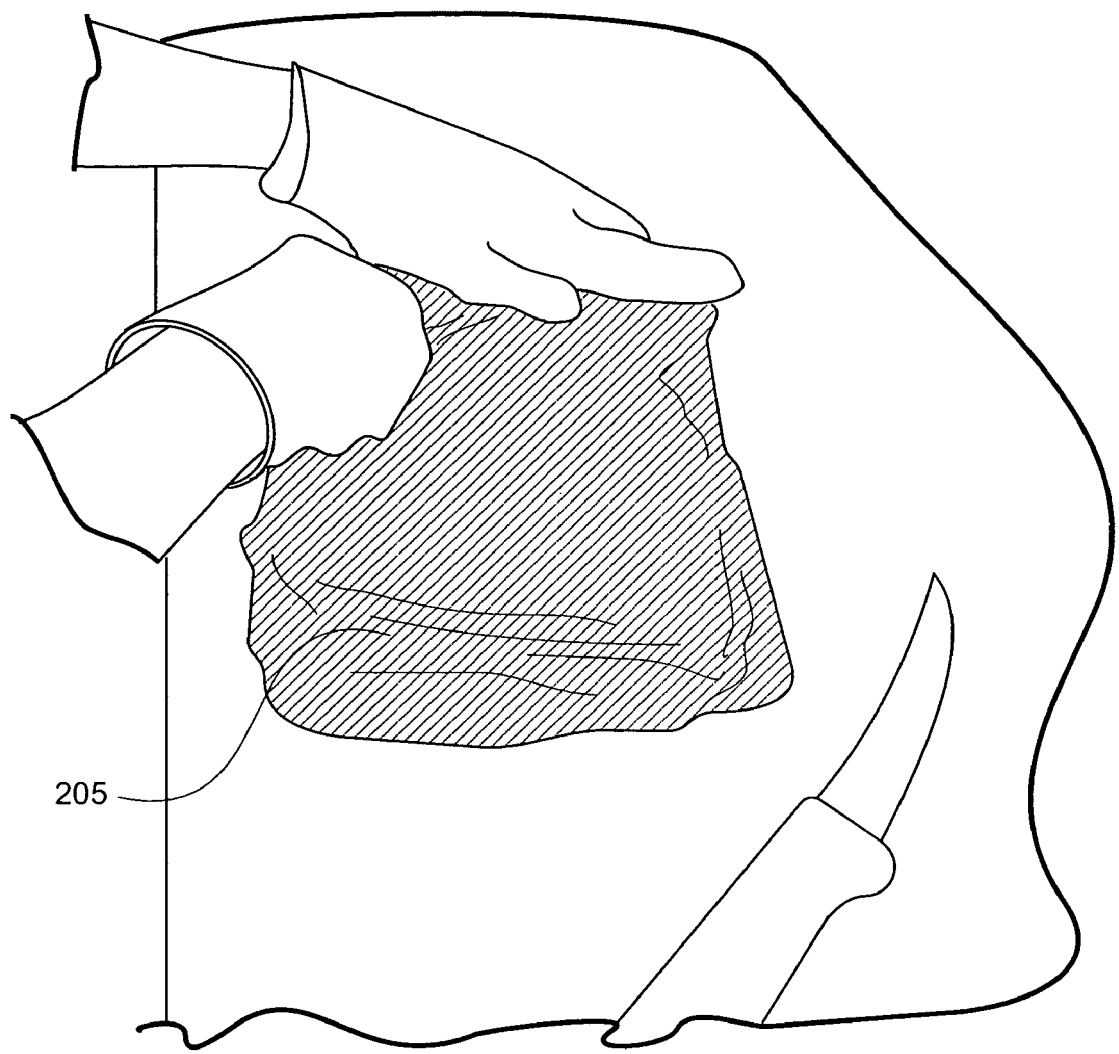
FIG. 2i shows the final cleaned pericardium sheet.

FIGS. 2h and 2i illustrates the procedure for obtaining a flat sheet of pericardium 205. This involves cutting along the pericardium 200, starting at the opening for the aorta, vena cava and pulmonary artery 204. The flat sheet of pericardium is shown in FIG. 2i.

Preferably before the "raw" pericardium is stretched over the mold it undergoes a pre-processing step. This pre-processing step involves holding the "raw" pericardium in a cold saline bath until the fat covering the pericardium has stiffened.

The method for processing bovine pericardium yields "clean" pericardium of higher quality than current processing methods. Current processing methods involve laying the "raw" pericardium upon a flat board and cutting, hacking and tearing the surface fat off. The blunt trauma exerted on the pericardial tissue can leave the pericardium mushy and useless for the implant and xenograft industry. This leads to a high rejection rate, since pericardial tissue needs to be firm and elastic for use in the xenograft industry and implant industry. The described apparatus and method for processing results in higher quality pericardium with lower rejection rates because the pericardium maintains its natural shape and elasticity during the fat removal process. This may be because the pericardium is stretched over the mold 100 and the mold 100 simulates the natural position of the pericardium. The mold 100 makes fat removal easier and results in firmer and higher quality pericardium with lower rejection rates.

The quality of "cleaned" pericardium is also related to the speed of the processing. Faster processing typically results in lower quality of the "cleaned" pericardium. The described method and apparatus allow for higher quality of "cleaned" pericardium to be produced at a faster rate than the existing methods of pericardium processing, or the described apparatus and method allow for higher quality "cleaned" pericardium to be produced within the same time it would take existing methods, or the described apparatus and method allow the same quality of "cleaned" pericardium to be produced but in significantly shorter time than the existing methods.

The invention claimed is:

1. An apparatus for use in processing "raw" pericardium comprising:
   a mold including a generally hemispheroid dome;
   a support base upon which the mold is mounted; and
   the hemispheroid dome having a diameter suitable for stretching a pericardium over the dome, the hemispheroid dome being a prolate hemispheroid dome constructed from sterilizable materials and suitable for use in an abattoir.

2. The apparatus as claimed in claim 1, wherein the hemispheroid dome having a diameter between 10 cm and 30 cm at the widest point.

3. The apparatus as claimed in claim 1, wherein the support base includes a spike extending from the support base.

4. The apparatus as claimed in claim 1, wherein the hole in the mold is centered about the major axis of the hemispheroid dome.

5. The apparatus as claimed in claim 1, wherein the support base is made from a dense material so as to provide the dome with stability.

6. The mold as claimed in claim 1, wherein the dome is rotatable on the support base about the major axis of the dome.

7. The apparatus as claimed in claim 1, wherein the hemispheroid dome is constructed from a material having a surface which provides some gripping force on tissue.

8. The apparatus as claimed in claim 1, wherein the mold is made of high density polyethylene.

9. A method for processing "raw" pericardium which comprises the steps;

stretching 'raw' pericardium over a mold such that the pericardium conforms to the shape of the mold and the mold stretches the pericardium;

separating at least some of the fat layer off the pericardial tissue layer where the pericardium is mounted over the mold;

removing fat from the total pericardium surface.

10. The method as claimed in claim 9 includes the step of cutting along the pericardium, starting at the opening for the aorta, vena cava and pulmonary artery, to obtain a flat sheet of pericardium.

11. The method as claimed in claim 9 includes the step of, before the raw pericardium is stretched over the mold, it is held in a cold saline bath until the fat covering pericardium has stiffened.

12. The method as claimed in claim 9, wherein a knife or hands are used to remove said fat layer from said pericardium.

13. The method as claimed in claim 9 includes rotating the mold to work the fat layer away from the pericardium progressively toward the arterial opening.

14. An apparatus for use in processing "raw" pericardium, said apparatus comprising:

a mold including a generally hemispheroid dome;

a support base upon which the mold is mounted; and the hemispheroid dome having a diameter suitable for stretching a pericardium over the dome, the dome being rotatable on the support base about a major axis of the dome and the mold being constructed out of sterilizable materials suitable for use in an abattoir.

15. The apparatus as claimed in claim 14, wherein the support base is made from high density polyethylene so as to provide the dome with stability.

16. The apparatus as claimed in claim 14, wherein the mold is mounted upon the support base and the support base includes a spike extending from the support base.

* * * * *